(12) United States Patent
Rump et al.

(10) Patent No.: US 9,421,364 B2
(45) Date of Patent: Aug. 23, 2016

(54) IMPLANTABLE ELECTRODE ARRANGEMENT FOR CARDIOLOGICAL DEVICES AND CARDIAC PACEMAKERS

(71) Applicant: BIOTRONIK SE & CO. KG, Berlin (DE)

(72) Inventors: Jens Rump, Berlin (DE); Heinrich Buessing, Berlin (DE); Michael Friedrich, Kleinmachnow (DE)

(73) Assignee: BIOTRONIK SE & CO. KG, Berlin (DE)

( * ) Notice: Subject to any disclaimer, the term of this patent is extended or adjusted under 35 U.S.C. 154(b) by 6 days.

(21) Appl. No.: 14/529,044

(22) Filed: Oct. 30, 2014

(65) Prior Publication Data

US 2015/0148879 A1   May 28, 2015

Related U.S. Application Data

(60) Provisional application No. 61/908,183, filed on Nov. 25, 2013.

(51) Int. Cl.
*A61N 1/08* (2006.01)
*A61N 1/05* (2006.01)
*A61N 1/37* (2006.01)

(52) U.S. Cl.
CPC .. *A61N 1/08* (2013.01); *A61N 1/05* (2013.01); *A61N 1/056* (2013.01); *A61N 1/3718* (2013.01); *A61N 2001/086* (2013.01)

(58) Field of Classification Search
CPC ........... A61N 1/08; A61N 1/05; A61N 1/056; A61N 1/3718; A61N 2001/086
See application file for complete search history.

(56) References Cited

U.S. PATENT DOCUMENTS

| | | |
|---|---|---|
| 6,123,660 A | 9/2000 | Leysieffer |
| 6,871,091 B2 | 3/2005 | Wilkinson et al. |
| 6,944,489 B2 | 9/2005 | Zeijlmeaker |
| 7,363,090 B2 | 4/2008 | Halperin et al. |
| 2004/0215279 A1 | 10/2004 | Houben et al. |
| 2008/0009905 A1 | 1/2008 | Zeijlmeaker |
| 2011/0137390 A1 | 6/2011 | Hill |
| 2012/0157813 A1 | 6/2012 | Doerr et al. |
| 2013/0150695 A1 | 6/2013 | Biela et al. |

FOREIGN PATENT DOCUMENTS

| | | |
|---|---|---|
| DE | 19840211 C1 | 12/1999 |
| DE | 102011086208 A1 | 5/2013 |
| EP | 2478932 A2 | 7/2012 |
| EP | 2602001 A1 | 6/2013 |

OTHER PUBLICATIONS

European Search Report received from EP Application Serial No. 14189633, dated Mar. 24, 2015, 6 pages.

*Primary Examiner* — Joseph Dietrich
(74) *Attorney, Agent, or Firm* — Arc IP Law, PC; Joseph J. Mayo

(57) ABSTRACT

An implantable electrode arrangement for cardiological devices, such as cardiac pacemakers, that includes an elongate electrode body with a proximal end and distal end, at least one electrode that contacts the body of the implant support and is arranged at, or in the vicinity of, the distal end of the electrode body. The implantable electrode arrangement includes at least one electric contact line that contacts the electrode, and an electromechanical resonance arrangement connected to the electrode or to a contact line to convert high-frequency signals irradiated into the electrode line into acousto-mechanical vibrations.

16 Claims, 2 Drawing Sheets

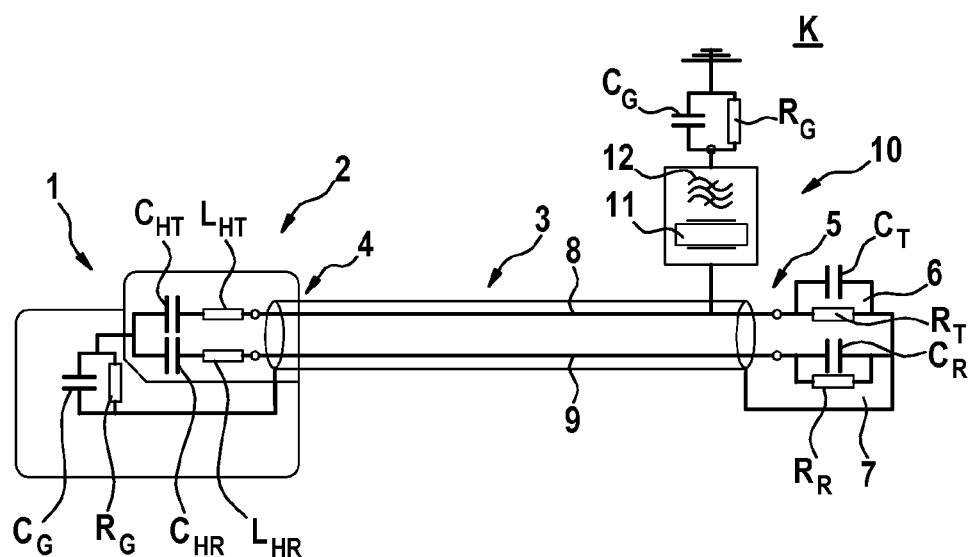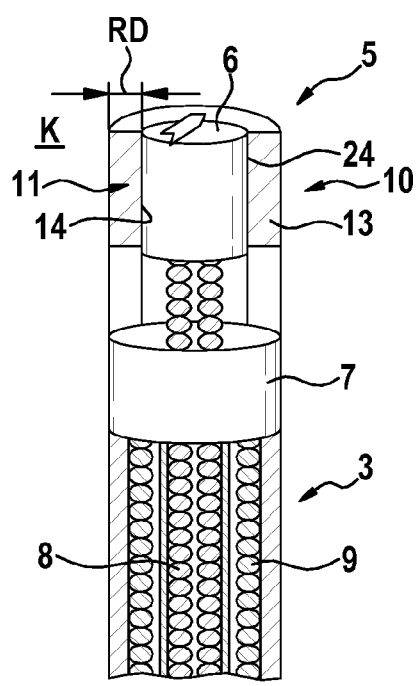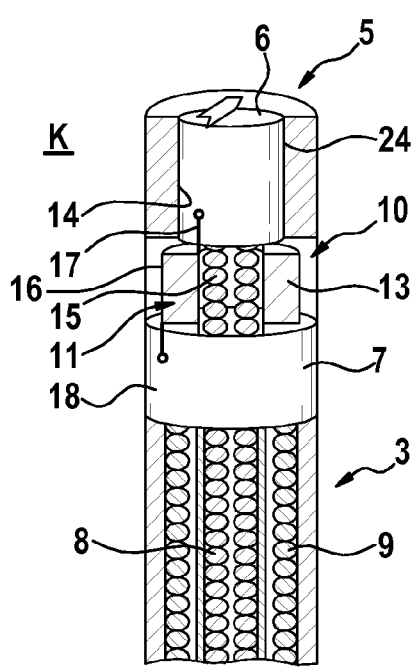

IMPLANTABLE ELECTRODE ARRANGEMENT FOR CARDIOLOGICAL DEVICES AND CARDIAC PACEMAKERS

This application claims the benefit of U.S. Provisional Patent Application 61/908,183 filed on 25 Nov. 2013, the specification of which is hereby incorporated herein by reference.

BACKGROUND OF THE INVENTION

1. Field of the Invention

Embodiments of the invention generally relate to an implantable electrode arrangement for cardiological devices, such as cardiac pacemakers, which includes an implant support body, an elongate electrode body with a proximal end and a distal end, at least one electrode with an electrode surface arranged in a region of the distal end of the electrode body and brought into contact with the implant support body, and at least one electric contact line that contacts the electrode.

2. Description of the Related Art

Generally, in the case of implantable electrode arrangements, contact line(s) acts or act similarly to an antenna in the event of irradiation of electromagnetic waves and convert the received energy into heat. A typical example of this problem is the examination of patients fitted with a cardiac pacemaker in magnetic resonance tomographs, which, besides a static magnetic field, also use a high-frequency alternating magnetic field superimposed thereby. If the implantable electrode arrangement is exposed to such an alternating magnetic field, signs of heating appear preferably at the ends of the contact lines running in the implant and are dependent on the amplitude of the irradiated electromagnetic wave and are maximal with formation of standing waves.

Various approaches are presented in prior art to solve the problem of heat appearing in the implant. For example, U.S. Pat. No. 7,363,090 entitled "Band Stop Filter Employing a Capacitor and an Inductor Tank Circuit to Enhance MRI Compatibility of Active Implantable Medical Devices", to Halperin et al., discloses filter arrangements in the feed line leading to a tip or ring electrode, the feed line being provided in the form of electromagnetic oscillating circuits that are constructed with the aid of conventional R-, C- and L-members. Due to the integration into the contact line, the filter elements of Halperin et al. inevitably influence the functionality of the electrode.

A further basic approach uses shunts, as is disclosed in United States Patent Publication 20080009905 entitled "Electrode System with Shunt Electrode" or U.S. Pat. No. 6,944,489 entitled "Method and Apparatus for Shunting Induced Currents in an Electrical Lead", both to Zeijlemaker, or U.S. Pat. No. 6,871,091 entitled "Apparatus and Method for Shunting Induced Currents in an Electrical Lead", to Wilkinson et al. For example, the shunt forms a branching off from the contact line, the branching being insulating for D.C. voltage signals but being able to conduct high-frequency signals due to its design, as is typically implemented by capacitor elements. As discussed in Zeijlemaker and Wilkinson et al, the contact line is thus coupled capacitively to the tissue surrounding the electrode arrangement, such that, in the event of irradiation of a high-frequency signal, the energy received by the contact line is delivered to the surrounding tissue, distributed via the shunt over a larger area. Since the nature of the energy of the irradiated signals is not converted, but in view of the capacitive coupling an electric alternating field is in turn generated, as disclosed in in Zeijlemaker and Wilkinson et al, the achievable dissipation rate for the irradiated energy is limited.

BRIEF SUMMARY OF THE INVENTION

One or more embodiments of the invention include an implantable electrode arrangement such that electromagnetic signals of higher frequency irradiated into the electrode line(s) may be converted more effectively and distributed in a manner compatible with the body.

At least one embodiment of the invention as claimed herein includes an electromechanical resonance arrangement connected to an electrode or contact line in order to convert high-frequency signals irradiated into the electrode arrangement into acousto-mechanical vibrations.

One or more embodiments of the invention convert the irradiated electromechanical energy into a completely different form of energy, such as mechanical energy in the form of sound waves, whereby energy may be dissipated in a manner very compatible with the body and gentle on tissue.

In at least one embodiment, the electromagnetic resonance arrangement may include a piezocrystalline resonance element. In one or more embodiments, the piezocrystalline resonant element includes electromechanical resonance bodies that may include ceramic materials with non-centrosymmetric point groups. Such piezocrystalline resonance elements, in at least one embodiment, may include a geometric dimensioning that corresponds to the half-wavelength of the acousto-mechanical vibrations in a frequency range from 10 MHz to 400 MHz. This frequency range, in one or more embodiments, is the typical bandwidth used for frequencies with such implantable electrode devices to overcome the limitations of high-frequency signals wherein a dissipation rate for the irradiated energy is limited. In at least one embodiment of the invention, odd-numbered multiples of the half-wavelength of the acousto-mechanical vibration may be used as a basis for the geometric dimensioning of the piezocrystalline resonance element. In one or more embodiments, a corresponding component, depending on the type of vibration, may include a diameter for example that corresponds to the half-wavelength of sound waves in the above-mentioned radio-frequency range.

In at least one embodiment, the piezocrystalline resonance element may be a sleeve-shaped piezocrystal element. In one or more embodiments, the sleeve-shaped piezocrystal element may be combined with electrode forms, such as a tip electrode with a lateral ring area, or a ring electrode itself.

In at least one embodiment, the ring thickness of such a sleeve-shaped piezocrystal element may include the half-wavelength of the acousto-mechanical vibration that may be used as a dimensional parameter. In one or more embodiments, the values for a 64 MHz sound wave with a wavelength of 200 μm of the pressure wave may lie for example at a resonance layer thickness of approximately 100 μm. In at least one embodiment, a wall thicknesses of the resonance layer thickness may be produced and may include the desired crystal structure.

By way of one or more embodiments, the electromechanical resonance arrangement may include a piezocrystalline film, such as films that include in part or completely PVDF (polyvinylidene fluoride), hereinafter referred to as PVDF films or polyvinylidene fluoride films. In at least one embodiment, PVDF is an opaque, semi-crystalline, thermoplastic fluoroplastic with piezoelectric properties.

One or more embodiments of the invention include a formation of a piezocrystalline film by the application of materials having piezocrystalline properties to a film using PVD (physical vapor deposition) methods.

Piezocrystalline resonance elements in film form, according to at least one embodiment, may include a layered structure composed of the piezocrystalline film and a metal layer. In one or more embodiments, the metal layer may be used as a connection surface of the resonance element. In at least one embodiment, the layered structure may be constructed in a sandwich design, wherein at least two alternating film and metal layers are provided.

A resonance element of an electrode arrangement, according to one or more embodiments of the invention, may be produced by winding the piezocrystalline film with the metal layer a number of times around a support, such as around a head sleeve of a tip electrode, so as to form the electromechanical resonance arrangement. In at least one embodiment, the outer metallization of the piezoceramic element then produces the electric contact to the body, such as bodily tissue or bodily liquids.

In one or more embodiments of the invention, the film/metal layered configuration, even when formed as a multiple winding, may be adequately contacted with the aid of or using a connecting lug.

One or more embodiments of the invention may include different circuit arrangements of the electromechanical resonance device, for example between an electrode or the electrode contact line and the implant support body of the implant support itself. In at least one embodiment, in the region of the distal electrode, the electromechanical resonance arrangement may be arranged externally on the head sleeve or internally on the head sleeve and/or within the head sleeve on a shaft to actuate an anchoring screw on the tip electrode.

In one or more embodiments, the electromechanical resonance arrangement may be arranged in a circuit between two electrodes of the electrode arrangement, such as between the tip electrode and the ring electrode. In one or more embodiments, the electromechanical resonance arrangement may be positioned beneath the ring electrode.

By way of at least one embodiment, the piezocrystalline resonance element may be produced completely or in part from one or more of the following materials: anisotropic $SiO_2$ (α-quartz glass), aluminum nitride, polyvinylidene fluoride, barium titanate, lithium niobates, gallium orthophosphates, berlinite, minerals of the tourmaline group, Seignette's salt and potassium-sodium niobate.

According to one or more embodiments, due to the selected electromechanical resonance elements and incorporation thereof in implantable electrode arrangements, the functional properties, such as with conventional direct signal operation of the electrodes, may not be destroyed by the measures described above. At the same time however, in at least one embodiment, an effective reduction of the heating at the end of the contact lines due to irradiated electromagnetic alternating fields may be achieved.

BRIEF DESCRIPTION OF THE DRAWINGS

The above and other aspects, features and advantages of at least one embodiment of the invention will be more apparent from the following more particular description thereof, presented in conjunction with the following drawings wherein:

FIG. 1 shows a schematic illustration of an implantable electrode device in the manner of an equivalent circuit diagram for the electric components, FIGS. 2 and 3 show schematic, partly cut-away views of the distal end of an electrode arrangement in one or more embodiments of the electromechanical resonance arrangement on the basis of a sleeve-shaped piezocrystal element.

DETAILED DESCRIPTION OF THE INVENTION

Figure 4:
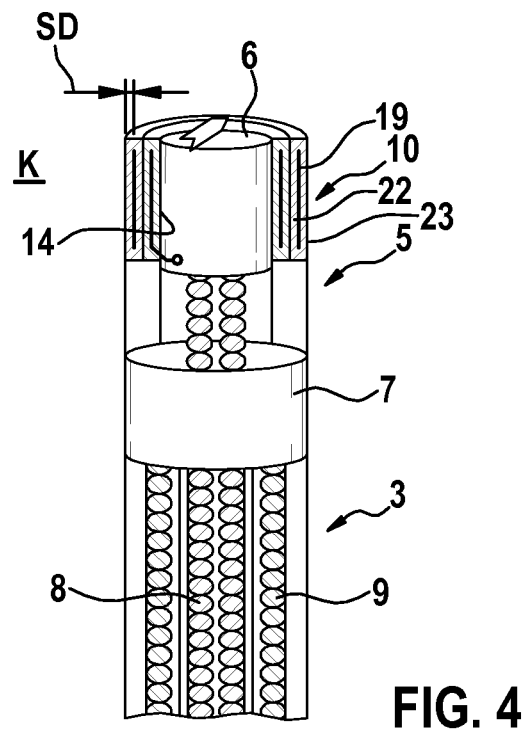
FIG. 4 shows a view of an electrode arrangement similar to FIG. 2 and FIG. 3 with a piezocrystalline resonance element on the basis of a piezocrystalline film.

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

FIG. 1 shows an implantable electrode arrangement with a schematically illustrated cardiac pacemaker 1, to the header 2 of which an elongate electrode body 3 is connected via its proximal end 4, according to one or more embodiments of the invention. At the distal end 5 of the electrode body 3, in at least one embodiment, a tip electrode 6 is located directly at the tip of the electrode body 1, and a ring electrode 7 is located therebehind in the proximal direction. In one or more embodiments, the helical contact lines 8 and 9 respectively for the tip electrode 6 and the ring electrode 7 may run in the electrode body 3.

FIG. 1, formed in the manner of an equivalent circuit diagram, shows, in the region of the header 2, the capacitive and impedance resistors $C_{HT}$, $L_{HT}$, $C_{HR}$, $L_{HR}$ to the contact lines 8, 9 and also the capacitive and ohmic resistors $C_G$, $R_G$ to the electrode body itself, according to one or more embodiments of the invention.

According to at least one embodiment, at the distal end 5 of the electrode body 3, the capacitive resistors $C_T$ and $C_R$ as well as the ohmic transition resistors $R_T$ and $R_R$ respectively of the tip and ring electrode 6, 7 are illustrated.

In one or more embodiments of the invention, an electromechanical resonance arrangement 10 may be connected to the contact line 8 of the tip electrode 6 and may include a piezocrystalline resonance element 11. In at least one embodiment, any high-frequency signals irradiated into the contact line 8 may excite the resonance element 11 to produce mechanical vibrations, such as sound waves 12, which may be delivered to the tissue. In one or more embodiments, the contact between electromechanical resonance device 10 and the tissue of the body in which the apparatus is implanted is represented by the capacitor $C_G$ or the ohmic resistor $R_G$ in the equivalent circuit diagram, as shown in the upper right portion of FIG. 1, wherein the tissue of the body is represented with the ground symbol while the case of the implantable device in the lower left portion of the figure forms another path to the tissue of the body.

As shown in FIG. 2, the electrode body 3 includes the tip and ring electrode 6, 7, at the distal end 5, according to one or more embodiments of the invention. The electromechanical resonance arrangement 10, in at least one embodiment, may include a sleeve-shaped piezocrystal element 13 on the lateral surface of the head sleeve 14 of the tip electrode 6. In one or more embodiments, the ring thickness RD of the piezocrystal element 13 may include the half-wavelength of the resonant pressure waves. In at least one embodiment, the high sound speeds within the crystalline ceramics of the piezocrystal element 13, for example of 10 km/s, may produce pressure wavelengths around 200 μm at a frequency of 64 MHz. In one or more embodiments, the resonant layer thickness and accordingly the ring thickness RD of the piezocrystal element 13 may be at least at 100 μm. In at least one embodiment, the generated sound waves 12 may be delivered into the body K in a compatible manner.

In one or more embodiments, as shown in FIG. 3, the sleeve-shaped piezocrystal element 13 may be arranged between the tip electrode 6 and the ring electrode 7 about the helical contact line 8. In at least one embodiment, the contact with the head sleeve 14 of the tip electrode or with the ring electrode 6 or 7 is achieved via corresponding contact surfaces 15, 16 on the inner and outer lateral surface respectively of the sleeve-shaped piezocrystal element 13 and via terminal connectors 17, 18. As such, according to one or more embodiments, any high-frequency electromagnetic signals irradiated into the contact lines 8, 9 may be converted into acousto-mechanical waves and the irradiated energy may be dissipated in a manner compatible with the body.

Figure 5:
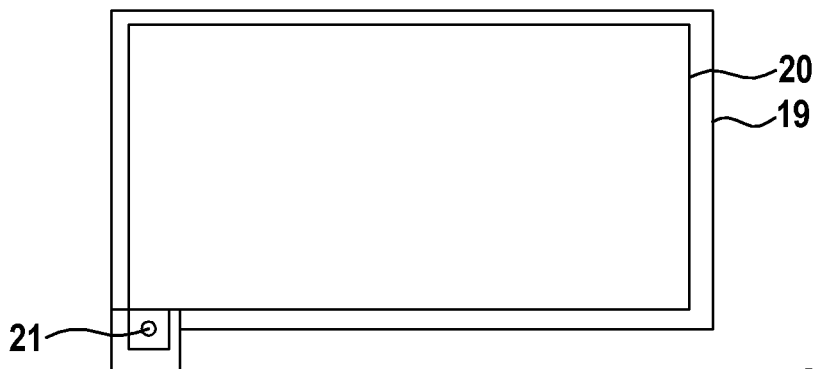
FIGS. 5 and 6 show a plan view and a section through a sandwich construction of a piezocrystalline film with metal layer for use in the electrode arrangement according to FIG. 4.
Figure 6:
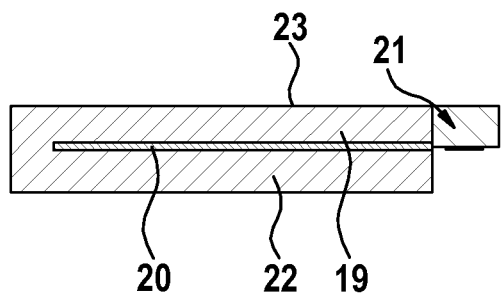

FIGS. 4 to 6 illustrate the piezocrystalline resonance element 11, which may be produced as a sandwich construction of a metallized piezocrystalline film, according to one or more embodiments of the invention. In at least one embodiment, a piezocrystalline film 19 may be provided on one side with a metallization coating 20, which is provided at one point with a connecting lug 21. A second layer of a piezocrystalline film 23, in at least one embodiment, may be fitted onto the metallization coating 20. In one or more embodiments, a further metallization coating 23 may be applied to one of the two exposed surfaces of the films 19, 22, for example to the upper surface of the film 19 as shown in FIG. 6. In at least one embodiment, the sandwich configuration may initially be connected in the region of the connecting lug 21 to the head sleeve 14 forming the tip electrode 6 in the region of the lateral surface thereof, and the sandwich construction may then wound be closely around the head such that the metallization coating 23 comes to rest externally and therefore produces the electric contact to the surrounding tissue or the blood in the body K of the implant support. According to one or more embodiments, the resonance effect may be influenced and the bandwidth of the frequencies of irradiated electromagnetic signals detectable therewith may adapt to the requirements accordingly as a result of the number of windings. In at least one embodiment, the piezocrystalline films 19, 22 may be produced by physical vapor deposition (PVD).

By way of one or more embodiments of the invention, the layer thickness SD of the piezocrystalline films 19, 22 may in turn correspond to the half-wavelength of the acousto-mechanical vibrations generated by the conversion of irradiated high-frequency signals.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable electrode arrangement for cardiological devices comprising:
    an elongate electrode body with a proximal end and distal end;
    at least one electrode configured to contact tissue of a body and is arranged at, or in the vicinity of, the distal end of the elongate electrode body;
    at least one electric contact line that contacts the at least one electrode; and,
    an electromechanical resonance arrangement comprising a piezocrystalline resonance element, wherein the electromechanical resonance arrangement is connected to the at least one electrode or the at least one electrical contact line that converts high-frequency signals irradiated into the implantable electrode arrangement into acousto-mechanical vibrations;
    wherein the piezocrystalline resonance element comprises a geometrical dimension that corresponds to a half-wavelength or an odd-numbered multiple of the half-wavelength of the acousto-mechanical vibrations in a frequency range from 10 MHz to 400 MHz.

2. The implantable electrode arrangement as claimed in claim 1, wherein the piezocrystalline resonance element comprises electromechanical resonance bodies comprising ceramic materials with non-centrosymmetric point groups.

3. The implantable electrode arrangement as claimed in claim 1, wherein the piezocrystalline resonance element is a sleeve-shaped piezocrystal element.

4. The implantable electrode arrangement as claimed in claim 3, wherein a ring thickness of the sleeve-shaped piezocrystal element corresponds to the half-wavelength of the acousto-mechanical vibration.

5. The implantable electrode arrangement as claimed in claim 1, wherein the piezocrystalline resonance element comprises a piezocrystalline film comprising polyvinylidene fluoride (PVDF).

6. The implantable electrode arrangement as claimed in claim 5, wherein the piezocrystalline film is covered by a metal layer.

7. The implantable electrode arrangement as claimed in claim 6, wherein the piezocrystalline film with the metal layer comprises a sandwich construction with at least two alternating film and metal layers.

8. The implantable electrode arrangement as claimed in claim 6, wherein the piezocrystalline film with the metal layer is wound a number of times around a support, wherein said support comprises a head sleeve of a tip electrode, to form the electromechanical resonance arrangement.

9. The implantable electrode arrangement as claimed in claim 7, wherein the piezocrystalline film with the metal layer is wound a number of times around a support, wherein said support comprises a head sleeve of a tip electrode, to form the electromechanical resonance arrangement.

10. The implantable electrode arrangement as claimed in claim 6, wherein the metal layer is provided with a connecting lug.

11. The implantable electrode arrangement as claimed in claim 7, wherein the metal layer is provided with a connecting lug.

12. The implantable electrode arrangement as claimed in claim 1, wherein the electromechanical resonance arrangement is arranged in a circuit between the at least one electrode or between the at least one contact line and the tissue of the body.

13. The implantable electrode arrangement as claimed in claim 1, further comprising a head sleeve in the region of the distal electrode, wherein the electromechanical resonance arrangement is attached externally on the head sleeve, or internally in the head sleeve, or within the head sleeve to a shaft, or forms a portion of the head sleeve.

14. The implantable electrode arrangement as claimed in claim 1, wherein the at least one electrode comprises two electrodes comprising a tip electrode and a ring electrode, and wherein the electromechanical resonance arrangement is arranged in a circuit between the tip electrode and the ring electrode.

15. The implantable electrode arrangement as claimed in claim 1, wherein the at least one electrode comprises a ring electrode, and wherein the electromechanical resonance arrangement is arranged beneath the ring electrode.

16. The implantable electrode arrangement as claimed in claim 1, wherein the piezocrystalline resonance element completely or partially comprises a material selected form one or more of anisotropic $SiO_2$ (α-quartz glass), aluminum nitride, polyvinylidene fluoride, barium titanate, lithium niobates, gallium orthophosphates, berlinite, minerals of the tourmaline group, Seignette's salt and potassium-sodium niobate.

* * * * *